(12) United States Patent
Carter

(10) Patent No.: US 8,360,590 B2
(45) Date of Patent: Jan. 29, 2013

(54) PLUMBING FIXTURE WITH LIGHT PIPE ILLUMINATION

(76) Inventor: Kip Carter, Temecula, CA (US)

( * ) Notice: Subject to any disclaimer, the term of this patent is extended or adjusted under 35 U.S.C. 154(b) by 258 days.

(21) Appl. No.: 12/543,055

(22) Filed: Aug. 18, 2009

(65) Prior Publication Data

US 2010/0046199 A1 Feb. 25, 2010

Related U.S. Application Data

(60) Provisional application No. 61/091,260, filed on Aug. 22, 2008.

(51) Int. Cl.
*F21V 33/00* (2006.01)
*G02B 6/42* (2006.01)

(52) U.S. Cl. ............... 362/96; 362/562; 362/565

(58) Field of Classification Search ............ 362/96, 362/101, 559, 562, 565, 576; 40/406, 407
See application file for complete search history.

(56) References Cited

U.S. PATENT DOCUMENTS

| | | | | |
|---|---|---|---|---|
| 1,225,865 A * | 5/1917 | Schneible | ............ | 40/332 |
| 1,926,945 A * | 9/1933 | Hipp, Jr. | ............ | 362/101 |
| 3,748,456 A | 7/1973 | Brien | | |
| 3,801,022 A | 4/1974 | Cassey | | |
| 4,241,868 A * | 12/1980 | Perkins | ............ | 236/12.11 |
| 4,556,933 A | 12/1985 | Mendoza | | |
| 4,661,893 A | 4/1987 | Robinson et al. | | |
| 4,749,126 A * | 6/1988 | Kessener et al. | ............ | 362/101 |
| 4,875,200 A | 10/1989 | Tillery | | |
| 4,881,280 A * | 11/1989 | Lesikar | ............ | 4/507 |
| 4,899,453 A | 2/1990 | Bhat et al. | | |
| 5,217,292 A * | 6/1993 | Chalberg | ............ | 362/96 |
| 5,680,730 A | 10/1997 | Epple | | |
| 6,375,342 B1 * | 4/2002 | Koren et al. | ............ | 362/562 |
| 6,692,132 B1 | 2/2004 | Meeker | | |
| 6,805,458 B2 * | 10/2004 | Schindler et al. | ............ | 362/96 |
| 6,957,452 B2 * | 10/2005 | Grant | ............ | 362/559 |
| 7,008,073 B2 * | 3/2006 | Stuhlmacher, II | ............ | 362/96 |
| 7,187,141 B2 | 3/2007 | Mueller et al. | | |
| 7,194,774 B2 * | 3/2007 | Bergstrom | ............ | 362/96 |
| 7,222,979 B1 | 5/2007 | Popowich et al. | | |
| 7,229,027 B2 * | 6/2007 | Ehresman et al. | ............ | 362/96 |
| 7,303,299 B2 * | 12/2007 | Theus | ............ | 362/96 |
| 7,374,323 B1 | 5/2008 | Kelman et al. | | |
| 7,384,165 B2 * | 6/2008 | Doyle | ............ | 362/101 |
| 7,389,020 B2 | 6/2008 | Dixon | | |

* cited by examiner

*Primary Examiner* — Alan Cariaso
(74) *Attorney, Agent, or Firm* — Berenato & White, LLC

(57) ABSTRACT

A plumbing fixture using an integrated light pipe wherein a multi-shot method of injection molding is used to apply transparent, light channeling plastic completely or partially over surface areas of parts used above and below the waterline in the spa, pool or recreational water industry. Light is provided to the transparent over-molded portion of parts via a lighting element that can be molded onto the specific parts to be lit or assembled as a separate component to a part. All parts to be lit are directly or serially wired to a power supply mounted within the major appliance housing and are operated by an appropriate control device. This unique multi-shot manufacturing method and approach to illuminating targeted components and/or features provides lighting effects in a way that is simple and rugged and well suited to the rigorous environment of recreational uses of plumbing fixtures and illumination.

11 Claims, 5 Drawing Sheets

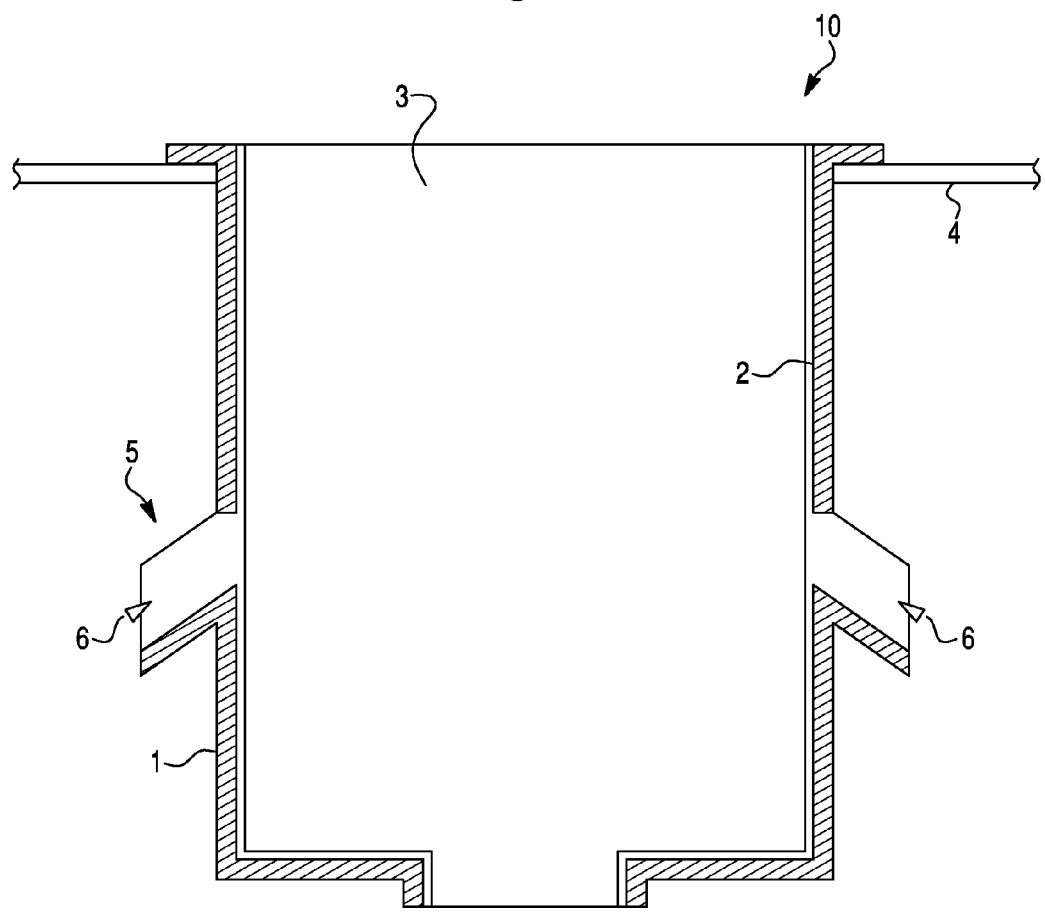

PLUMBING FIXTURE WITH LIGHT PIPE ILLUMINATION

This application claims the benefit of U.S. provisional Application No. 61/091,260, filed Aug. 22, 2008.

BACKGROUND OF THE INVENTION

1. Field of the Invention

The present invention relates generally to the field of illuminated plumbing fixtures. More specifically, the present invention is a plumbing fixture including a molded in place integrated light pipe feature for components used both above and below the waterline in spas, pools and all related recreational water products

2. Background

Plumbing fixtures combining illumination have likely been known since illumination has been known. Roman baths combined effective uses of daylight and torch light and reflection to illuminate otherwise unlit rooms and bathing hardware. With the advent of pressurized fountain works, public and private pools, etc, many lighting elements have been incorporated into bathing and water related displays.

The primary shortcoming of prior combinations of plumbing and light has been cost and durability. A light is somewhat more subject to failure when exposed to the rugged environment of a pool or spa or fountain and protecting the water tight integrity of the light creates cost and complication. If the integrity of the light and/or electrical source is compromised serious complications can result, including inadvertent electrocution.

SUMMARY OF THE INVENTION

The present invention overcomes the drawbacks of the prior art by combining simplicity and ruggedness into a single feature adaptable to a variety of plumbing fixtures. In its most basic form, this device includes the following components: 1) a part geometry (or shape) otherwise known as the Substrate (or $1^{st}$-shot) which may include all exposed plumbing fixture parts used in the spa/pool industry, (i.e. Jet Body/Face, Bezels, etc.); 2) the Decoration Layer (optional) layered onto the underlying substrate; and, 3) the Integrated Light Pipe (or $2^{nd}$-shot) is a clear/clear tinted/clear colored/semi-clear plastic which is molded over (or encapsulates) a partial or complete surface area of the substrate.

The light pipe, or translucent molded, layer functions as an integrated light pipe and thusly allows an applied light to be dispersed from a photo-connected light source across the part either partially or completely. The light pipe or translucent molded layer is applied over the substrate and/or the decorative layer using various forms of injection molding but preferably multi-shot molding or pre-mold/over-mold molding. The lighting element would use a light source, either colored or non-colored, such as but not limited to L.E.D., Laser, Fiber Optic, Incandescent or similar but preferably L.E.D. and Fiber Optic. Lastly, a power supply is necessary to provide electricity to the wired lighting element, The power supply could be a low voltage power supply (or battery, in the case where portability is necessary or desirable) that could provide electrical power to one (1)or any number of lighting elements and, thus, part(s).

The present invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

BRIEF DESCRIPTION OF THE DRAWINGS

FIG. 3 illustrates a schematic sectional view of a spa part showing the integrated light pipe feature and a molded lighting element.

DETAILED DESCRIPTION OF THE INVENTION

Figure 1:
FIG. 1 illustrates a schematic sectional view of a spa part trim element incorporating the integrated light pipe feature of the present invention.

With reference to the drawing Figures: FIG. 1 illustrates a sectional view of a spa part 10, in this case a Jet Face, showing the substrate ($1^{st}$-shot) 1, decoration layer 2, integrated molded light pipe translucent layer feature ($2^{nd}$-shot) 3 and barrier wall 4 (of the associated spa, pool, tub, etc.) that the part 10 would be mounted against. Although 10 is shown as a Jet Face, other exposed plumbing fixtures could be similarly equipped.

Figure 2:
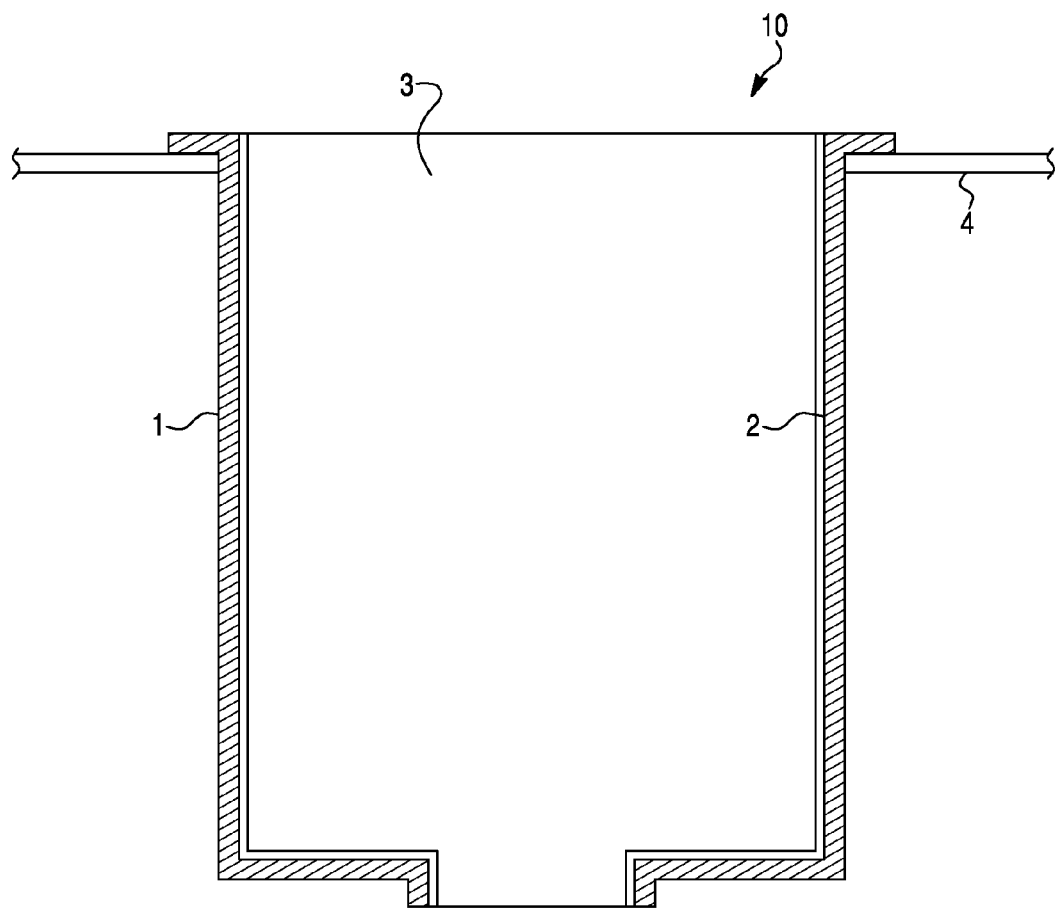
FIG. 2 illustrates a schematic sectional view of a spa fixture body part showing the integrated light pipe feature.

FIG. 2 illustrates a sectional view of another spa part 10, in this case also a Jet Body, but with a lighting element not integrally molded. FIG. 2 shows the plumbing component substrate ($1^{st}$-shot) 1, decoration layer 2, integrated light pipe feature ($2^{nd}$-shot) 3 and the barrier wall 4 (i.e., tub wall, etc.) that the part 10 would be mounted against. FIG. 3 illustrates a similar sectional view, as compared to FIG. 2, of a spa part 10, in this case also a Jet Body, but with the lighting element 6 array molded integrally to the jet body. FIG. 3 shows the substrate ($1^{st}$-shot) 1, decoration layer 2, integrated light pipe feature ($2^{nd}$-shot) 3 and barrier wall 4 that the part 10 would be mounted against.

Figure 4A:
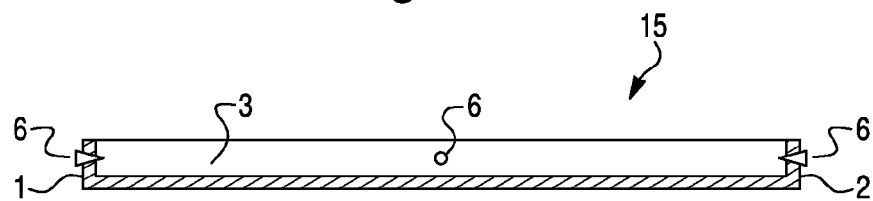
FIGS. 4A and B illustrate two schematic sectional views of a uni-directional lighting element, with and without a power cord.
Figure 4B:
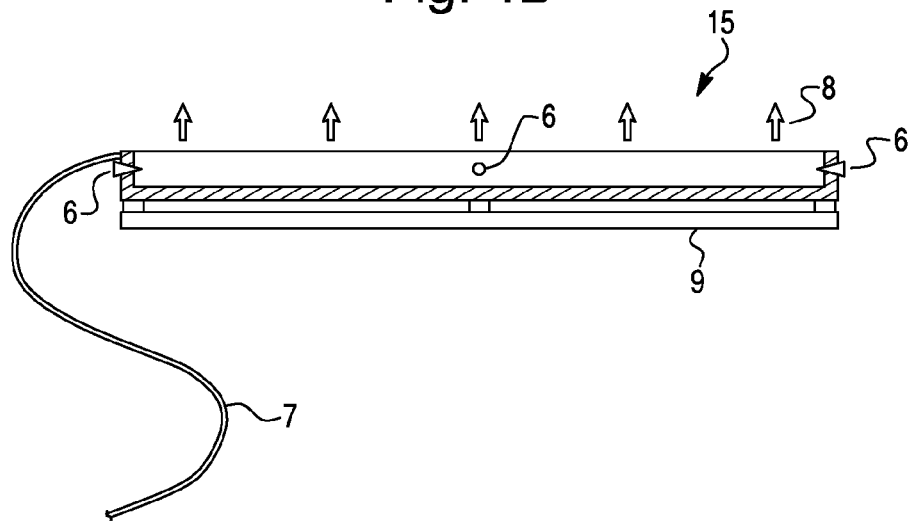

FIGS. 4A and B illustrate two (2) sectional views of a unidirectional lighting element array 15 having lighting elements 6 included therein. FIG. 4B shows a partial section of an annular multiple light source array 15 with a power cord 7, and FIG. 4A shows the array 15 without the power cord attached, both arrays 15 showing 3 light sources 6. The light provided by each array 15 is generally directed as indicated by arrows 8 upwardly from the lighting array 15 and into a light piping feature 3 associated with a given light pipe equipped fixture. The device in FIG. 4B further includes a PC Board 9, as may be required for certain types of light array control (i.e., LED, or sequencing, dimming, etc.). Each array 15 also shows the substrate ($1^{st}$-shot) 1 and integrated light pipe feature ($2^{nd}$-shot) 3.

Figure 5:
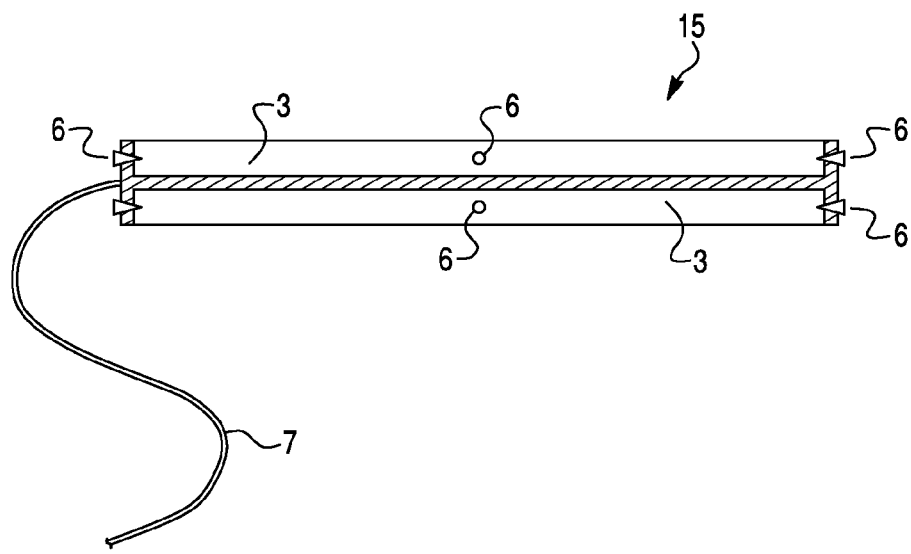
FIG. 5 illustrates a schematic sectional view of the multi-directional lighting element, with a power cord.

FIG. 5 illustrates a sectional view of the annular multi-directional lighting element array 15, with a power cord 7, using 3 light sources 6, and showing the substrate (1$^{st}$-shot) 1 and integrated light pipe feature (2$^{nd}$-shot) 2. The FIG. 5 array 15 would be used when light needs to be provided in each direction into a multi ported fixture with several light pipe equipped exposed portions. The array 15 is a 2$^{nd}$ shot of light piping material with lights 6 embedded therein or attached thereto. The array 15 is shown as an annular shape, but can be any shape complementary to an associated light piping element associated with a fixture. Thusly, the array 15 could be arced, straight, segmented, etc. in accord with an associated light pipe light receiving interface.

Figure 6:
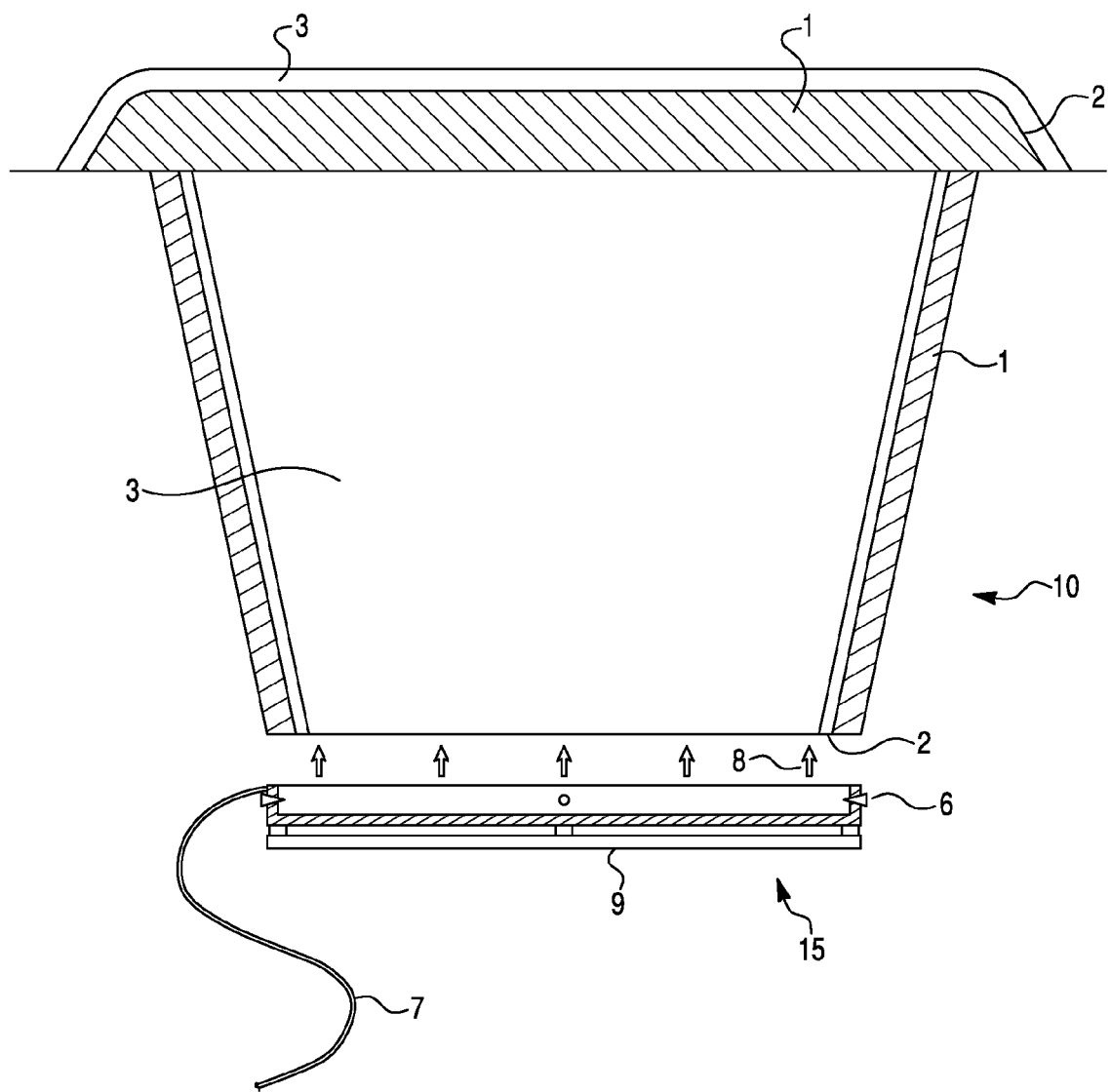
FIG. 6 illustrates a simplistic, non-detailed, schematic sectional view of a large Jet Face, including a uni-directional lighting element which is not integrally molded.

FIG. 6 illustrates a simplistic, non-detailed sectional view of a large Jet Face 10, including a uni-directional lighting element which is not molded into the Jet face body itself but is, instead, separately associated and attached. The lighting array 15 showing 3 light sources 6. This array 15 combines the FIGS. 1 and 4 features to create a complete installable part 10 assembly.

Figure 7:
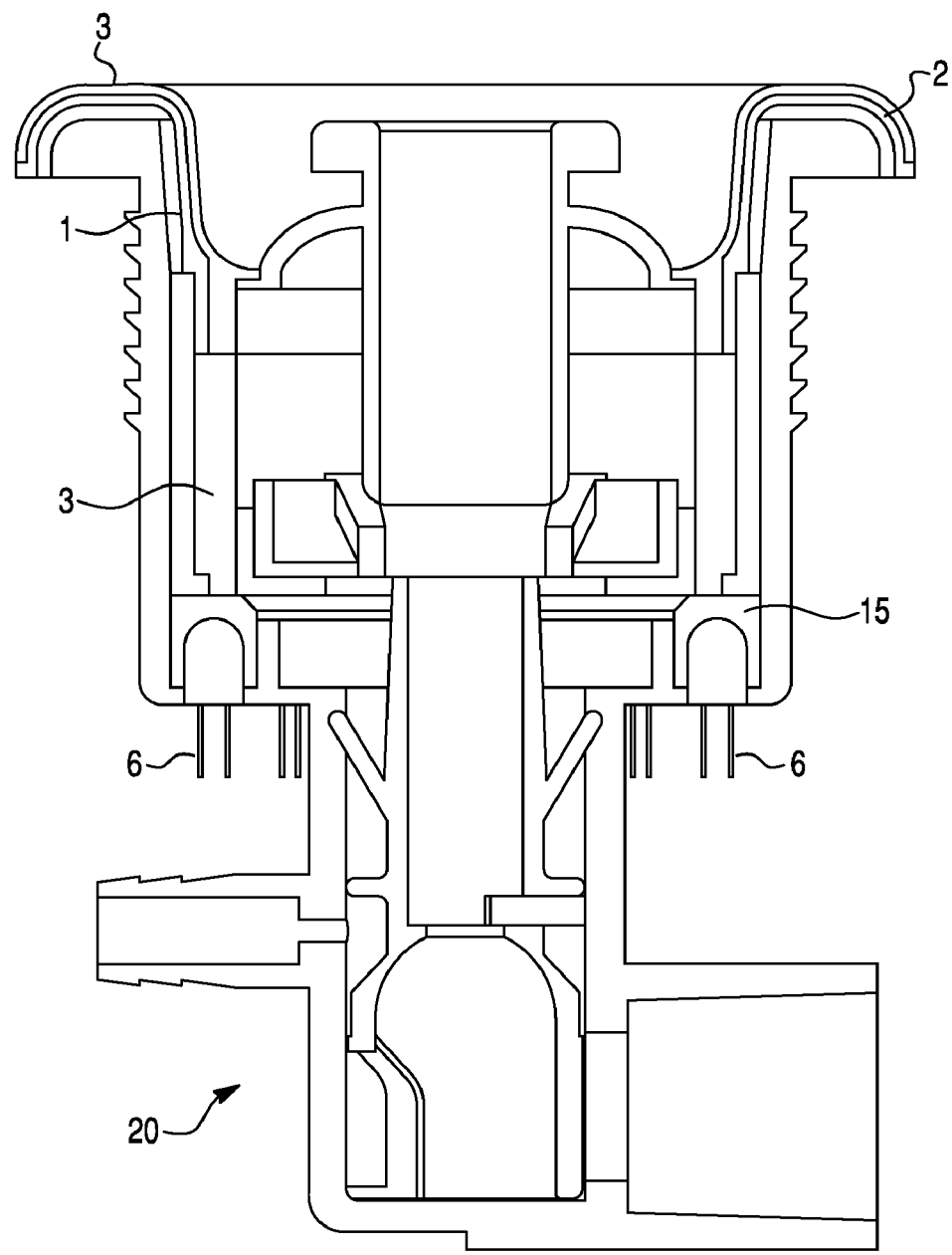
FIG. 7 shows a sectional view of the light pipe feature according to the present invention incorporated into an actual plumbing fixture.

FIG. 7 shows a partial sectional view of an actual plumbing fixture jet 20. The jet 20 is equipped with a molded substrate 1, overlying decorative layer 2, and a light pipe layer 3 layered onto the decorative layer. The light pipe is illuminated by lights 6 (LED type shown) in annular array 15, each light 6 wired to a control system for providing suitable electric power/control to provide illumination.

The light pipe 3 is illuminated using a wired lighting element array 15 that can be attached in a number of known or conventional ways. Such methods of attachment would include, but would not limited to: being threaded onto its mating part; molded directly into the geometry of a particular part; glued into place; press fit into place; heat staked into place and/or sonically welded into place which would make a complete assembly (i.e. Substrate, Decoration Layer, Integrated Light Pipe and wired Lighting Element) as shown in FIG. 7.

The decorative layer 2 can be applied (but does not have to be present if the underlying substrate is suitable to purpose) by various means such as but not limited to: paint; water immersion; sublimation; and, films applied to the surface of the substrate to enhance the overall look of the finished part(s) when lit or unlit The layer 2 may include but is not limited to: various solid colors; intricate artwork; theme related graphics; unique or varied patterns; metallic's; texture or fabric looks; photographic images; and, any type of graphical decoration that can be added to a part prior to molding the integrated light pipe feature into place.

The foregoing components are connected as follows: the power supply 7 is electrically connected to every lighting element 6 that will be lit (illuminated) via a direct and/or serial wiring system which runs throughout the entire appliance/structure and will in turn provide constant and regulated electrical power to each lighting element and the attached part(s). Light 8 is transmitted up and through the molded in place integrated light pipe translucent molded layer 3, past the barrier wall 4 of the appliance/structure and is dispersed across a partial or complete exposed surface area of the targeted part(s) 10 and 20. The part(s) 10 and 20 can be illuminated with various forms of lighting such as, but not limited to: bright light; low light; soft glowing light and/or colored light, both above and below the water line for a complete or partial illumination effect. This effect is currently not available in the spa, pool and related recreational water industries at this time or via this integrated light pipe technology using molding technologies known primarily as multi-shot molding and/or pre-mold/over-mold molding.

It should further be noted that: A) this technology could also include but is not limited to different designs, shapes, sizes, diameters, surface and subsurface textures and colors, on either the substrate, which could also be translucent, or the integrated light pipe or all other targeted parts; B) the construction of the lighting elements can be varied such as but not limited to the lighting element being either molded directly into a part(s) at various locations and/or angles on the part(s) thus allowing the light pipe feature to channel light to specific part(s) when assembled, or as an individually molded lighting element which can be either a uni-directional or multi-directional lighting element and can then be assembled to the finished molded part(s) and any associated mating part(s) in any number of aforementioned ways (to form the complete assembly) and could utilize multiple lighting technologies such as but not limited to: L.E.D.; Laser; Incandescent; Fiber Optics; Colored Lighting; Strobe Lighting; LCD; Halogen; Fluorescent and other commonly used lighting sources found within the general lighting industry. The included lighting element(s) preferably being controlled with various types of switches/controls including, for example, rheostat controls. The quantity, angle, location, layout, direction or installation location of lights may be changed to create unique and/or different lighting effects; C) whereas chemical environments in the spa and pool industry are often caustic and/or corrosive, various types of clear/clear tinted/clear colored/semi-clear and opaque thermoplastic materials should be used for the substrate such as but not limited to commodity and/or engineered plastic resins commonly known as ABS, ASA, PVC, PMMA but preferably the plastic resins would be ABS, ASA and PMMA; D) whereas chemical environments in the spa and pool industry are often caustic and/or corrosive various types of clear/clear tinted/clear colored/semi-clear thermoplastics can be used for the integrated light pipe such as but not limited to commodity and/or engineered plastic resins commonly known as ABS, ASA, PMMA, SAN, TPU but preferably the plastic resins would be PMMA, ABS, ASA and would be applied using a multi-shot molding or pre-mold/over-mold molding technology; E) it should be further noted that the use of common materials and/or additives such as but not limited to: nitrogen; air; foaming agents; colorants; glitters; and, specialty additives can create unique and different looks, colors and/or light emission effects; F) additionally, unique processing techniques such as but not limited to fluctuating injection pressures, injection speeds and injection holding pressures will also create unique and different looks such as but not limited to: entrained bubbles; streaks; bursts; striations; and check marks within the integrated light pipe to add unique and different light emission effects; G) or the use of design features molded directly into the integrated light pipe such as but not limited to: bumps; ribs; dimples; undulations; nicks; scallops; textures; etc. can be added for unique light emissions or looks when the parts are lit and not lit and which is not currently available in the spa and pool industry at this time; H) the Decoration Layer can utilize various methods of decoration such as but not limited to: painted graphics; water immersion graphics; sublimation graphics; vacuum metalizing; metal plating and graphical films all of which would consist of specific or random graphics, which said graphics are applied to the substrate prior to the light pipe (transparent plastic) being molded into place and which said decoration techniques and methods are currently not in use in the spa and pool industry but the preferred methods would be painted graphics, water immersion graphics, sublimation graphics and graphical films; and, I) furthermore, it should be noted that depending on the specific design of a particular part and the desired effects to be accomplished the integrated light pipe can be molded to both the inside and outside geometry of a part that would be viewable during use. The substrate of the part having the integrated light pipe molded thereover, as mentioned above, may also be translucent.

Though primarily intended for the spa and pool industry, this technology could also be adapted to all forms of recreational and/or non-recreational water applications. For example, lighting the jet inlets/outlets of recreational water craft, water jets associated with underwater propulsion systems for divers, etc. Such a light feature might become a safety issue so as alert those nearby that a jet/suction device was active or about to become active.

While it has been described in terms of specific embodiments, it is to be understood that the invention is not limited to those embodiments. This invention may be embodied in many different forms and should not be construed as limited to the embodiments set forth herein; rather, these embodiments are provided by way of illustration only and so that this disclosure will be thorough, complete and will fully convey the full scope of the invention to those skilled in the art. Indeed, many modifications and other embodiments of the invention will come to mind of those skilled in the art to which this invention pertains, and which are intended to be and are covered by both this disclosure, the drawings and the claims.

The invention claimed is:

1. A continuously submerged illumination device comprising:
   a molded substrate having an exposed surface formed as a curved surface and adapted to face a body of water and an inside surface sealed from said body of water;
   a translucent light transmitting layer molded so as to overlie said substrate, said light transmitting layer including a light piping element in photo connection with a translucent over-molded surface shape portion of said translucent light transmitting layer that covers said exposed surface of said molded substrate, said translucent over-molded surface shape portion adapted to face said body of water;
   a lighting element mounted at said inside surface and providing light to said light piping element and over said exposed surface of said molded substrate, said lighting element passing through said inside surface and in photo connection with said translucent light transmitting surface; and
   a power supply connected to and providing electrical power to said lighting element, wherein when said lighting element is lit, light spreads through said light piping element and over said exposed surface of said molded substrate.

2. The fixture of claim 1, wherein: said substrate is translucent.

3. The fixture of claim 1, wherein: a decorative layer is applied to said molded substrate.

4. The fixture of claim 3, wherein: said decorative layer is colored film.

5. The fixture of claim 3, wherein: said decorative layer is a graphic applied using a water immersion technique.

6. The fixture of claim 3, wherein: said decorative layer is a graphic applied using a sublimation technique.

7. The fixture of claim 3, wherein: said decorative layer is painted.

8. The fixture of claim 1, further comprising: a PC board for controlling operation of said lighting element.

9. The fixture of claim 1, wherein: said lighting element is a molded integrally to said light piping element.

10. The fixture of claim 1, wherein: said lighting element includes more than one light source.

11. A continuously submerged illumination device comprising:
    a molded substrate forming an annular body, said annular body adapted to be submerged in water, said molded substrate having an exposed surface formed as a curved surface and adapted to face a body of water and an inside surface sealed from said body of water;
    a translucent light transmitting layer molded so as to overlie a portion of said substrate, said light transmitting layer defining a complimentary annular portion matching a shape of said annular body and adapted to be submerged in water;
    a lighting element providing light to said light transmitting layer over said exposed surface of said molded substrate, said lighting element being mounted at said inside surface and providing light to said light piping element and over said exposed surface of said molded substrate, wherein the lighting element passes through said inside surface and in photo connection with said translucent light transmitting surface; and
    a power supply connected to and providing electrical power to said lighting element, wherein when said lighting element is lit, light spreads through said light transmitting layer and over said exposed surface of said molded substrate.

* * * * *